Figure 1:
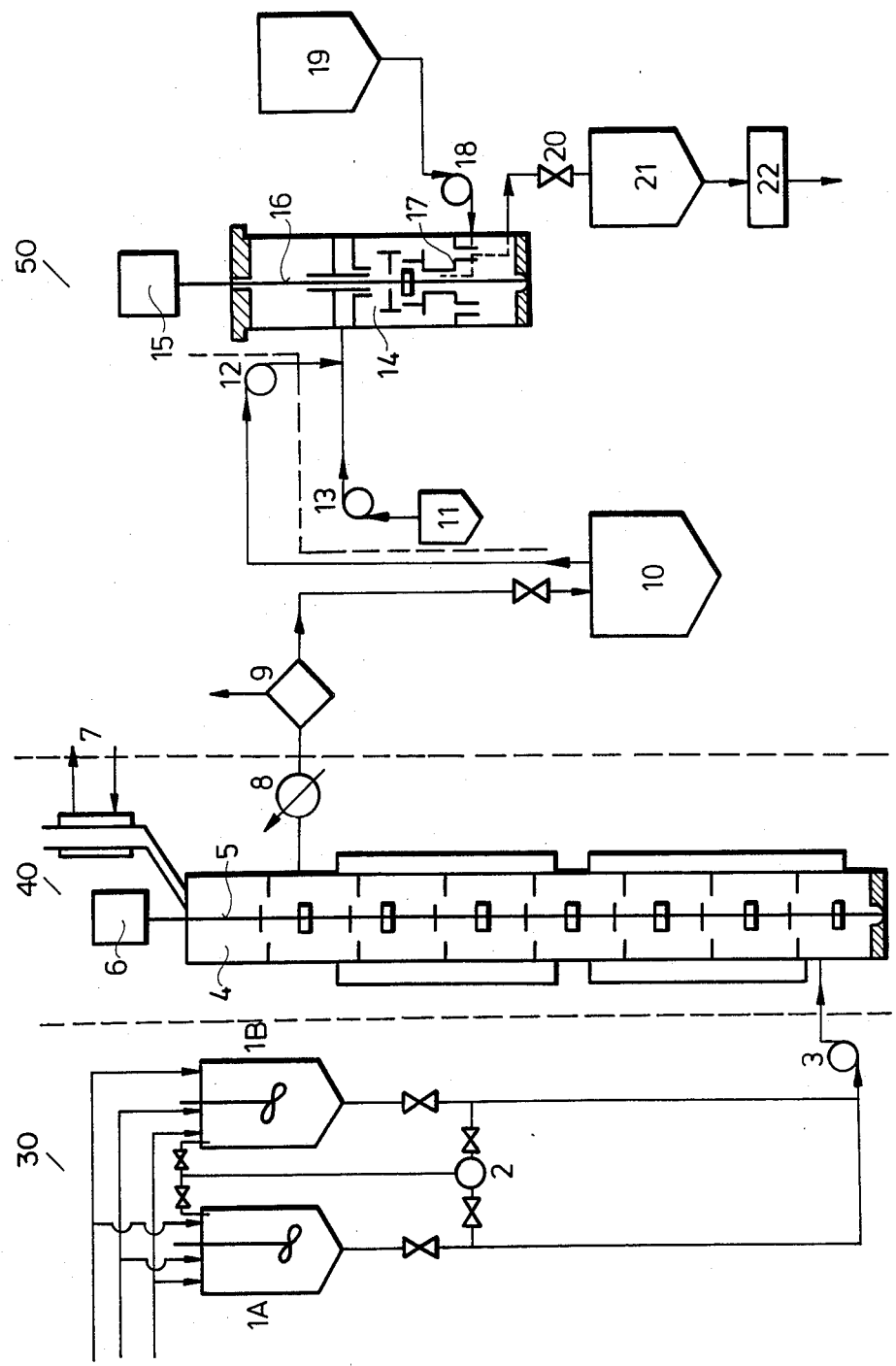

United States Patent [19]

Hevesi et al.

[11] Patent Number: 4,624,419

[45] Date of Patent: Nov. 25, 1986

[54] APPARATUS FOR PREPARING AQUEOUS AND OILY, SULFUR CONTAINING PRODUCTS

[75] Inventors: Jenö Hevesi; János Gyapai; Gábor Szudy; Bálint Nagy; Árpád Vágó; Ádámné N. Gesztelyi; József Keszler, all of Veszprém, Hungary

[73] Assignee: Nehézvegyipari Kutató Intézet, Veszprém, Hungary

[21] Appl. No.: 610,534

[22] Filed: May 15, 1984

[30] Foreign Application Priority Data

May 27, 1983 [HU] Hungary ............................. 1878/83

[51] Int. Cl.$^4$ ................... B02B 5/02; B01F 15/06; B01F 13/00
[52] U.S. Cl. ............................. 241/101 B; 366/145; 366/149; 366/279
[58] Field of Search ............... 366/297, 144, 145, 146, 366/147, 148, 149, 235, 348, 349, 241, 279, 22, 23, 24; 241/101 B

[56] References Cited

U.S. PATENT DOCUMENTS

| | | | |
|---|---|---|---|
| 4,183,675 | 1/1980 | Zarow | 366/144 |
| 4,194,842 | 3/1980 | Puthawala | 366/145 |
| 4,325,641 | 4/1982 | Babus | 241/101 B |
| 4,471,916 | 9/1984 | Donaldson | 241/101 B |

*Primary Examiner*—Robert W. Jenkins
*Attorney, Agent, or Firm*—Gabriel P. Katona

[57] ABSTRACT

The invention relates to a process for producing aqueous and oily, sulfur containing products.

The invention also relates to an apparatus for producing aqueous and oily, sulfur containing products, which comprises a feeder, mixing unit and a unit for separating the liquid and solid phases. In the process a dispersion is prepared from lime sulfur solution, a surface active material and oil.

In the apparatus the feeder includes a wet mill, the charging pump delivering the suspension thus obtained, the mixing unit is provided with a heating jacket, agitator, a cooler and a unit for separating the liquid and solid phases. The apparatus comprises a further mixing unit with a storage tank equipped with a charging pump and dispergator. The feeder, the mixing unit and the further mixing unit are interconnected by pipes.

4 Claims, 1 Drawing Figure

APPARATUS FOR PREPARING AQUEOUS AND OILY, SULFUR CONTAINING PRODUCTS

The invention relates to a process for preparing aqueous and oily, sulfur containing products.

The invention also relates to an apparatus for preparing oily and aqueous, sulfur containing products, provided with a feeder, a mixing unit, as well as a unit separating the liquid and solid phases.

Various pesticides are known, which, among others, can be used as washing sprays for plants in the wintertime or as summertime sprays for the protection of fruits as apples, peaches, plums etc. as well as against grapevine fungi in particular powdery mildew and parasites as shield scales and mites. Mostly aqueous and oily, sulfur containing products have been used for these purposes.

It is a well known fact that the aqueous solution of calcium polysulfides—the product known under the name lime sulfur solution—is made of burnt lime, powdered sulfur and water by cooking at a proper temperature.

Depending on the proportion of the components of the lime sulfur solution, as well as on the circumstances of cooking, the solutions show considerably variable compositions and biological efficiency. The quantity and filtrability of the solid byproducts which can be removed by decanting or separation in any other manner, all depend on the reaction parameters.

The commercial production of lime sulfur solutions has been carried out in the prior art by batchwise production techniques. U.S. Pat. No. 1,434,266 discloses the pressurized operation of duplicators (steam jacketed evaporators) provided with an agitator.

In the course of producing lime sulfur solution by a batch process, cooking used to be performed "cautiously" since the excess of lime and overly long cooking influences quantity and filtrability of the solid byproducts, and these latter two parameters may influence the fitotoxic effect of the product, its general efficiency and other properties.

A further difficulty arising during batchwise processing is the foaming which takes place during cooking, resulting in changing concentration and requiring fresh water supply. It becomes clear from the statement of these problems that for the production of reproducible polysulfide-sulfur containing products of good quality practical experience and special knowledge are both indispensible.

A further problem is that the lime sulfur solution cannot be stored, as it reacts with the oxygen and carbon dioxide content of the air and quickly decomposes, accompanied by sulfur segregation. The lime sulfur solution that is produced has to be used without delay, otherwise the material is ruined.

It is well known that the storage stability of lime sulfur solution can be increased, i.e. the duration of its usefulness can be prolonged by covering the filtered solution with an oil layer.

The aim of the invention is to eliminate the aforesaid deficiencies and to provide an improved apparatus for the production of aqueous and oily sulfur containing products on an industrial scale, to be able to operate with a far better efficiency, than previously.

A further aim of the invention is to produce an aqueous and oily sulfur containing product, which is not harmful for vegetation and can be diluted and sprayed in compliance with requirements and, compared to known lime sulfur solutions and oil products, shows an increased pesticide effect, its oil component has a lesser tendency for segregation and in addition, it has a better storage stability.

Another aim of the invention is to provide an apparatus which has a feeding, a mixing unit, as well as a unit separating the liquid and the solid phases, and which is provided with structures for wet-milling, cooking, cooling and filtering the suspension and which is provided with a unit homogenizing the aqueous and oily components.

The invention is based on the recognition that the lime sulfur solution is dispersed with nonfitotoxic oil in the presence of a surface active material.

The process of the invention is realized by producing a dispersion from the lime sulfur solution, the surfactant and the oil.

From the point of view of keeping sulfur content at the required level it seems advantageous that the density of the lime sulfur solution to be in the range between 1.25 and 1.35 $g/cm^3$, expediently 1.295 and 1.305 $g/cm^3$.

To obtain stable and thus well storable products, as well a proper wetting of the spray in the course of application, it is expedient to use a surface active material of anionic and/or nonionic type, in a proportion of 0.5–25.0 weight % related to the total quantity of the products according to the invention.

An oil of nonfitotoxic character is used to prolong the duration of applicability of the product.

Suitably a ratio of lime sulfur solution and oil of 1:1–1:9, advantageously 1:1–1.4, related to the total weight of the product according to the invention is used for improved stability and shelf life of the finished product, and to achieve biological efficiency.

The apparatus of the invention has a feeding unit for wet grinding the components, and a charging pump delivering the suspension obtained. The mixing unit of the apparatus comprises a heating jacket, an agitator, a cooler and a unit separating the solid and liquid phases respectively, and there is at least one further mixing unit, wherein the storing tank is provided with a charging pump supplying the surface active material, as well as an oil tank also provided with a charging pump, and the dispersing mixing unit; the feeding, the mixing unit and the second mixing unit are interconnected by pipes.

In order to prevent water losses resulting from heating, a preferred embodiment is provided with a reflux condenser. For the sake of continuous operation, the independent operation of the two mixing units and for increased operational stability, it is advantageous to arrange between the mixing unit and the second mixing unit a buffer tank and a charging pump connected between the buffer tank and the second mixing unit. To ensure continuous operation of the apparatus an embodiment can be realized in which the further mixing unit is connected to a tank which is collecting and storing the aqueous and oily, sulfur containing product.

The process according to the invention will be detailed by means of an example of realization.

Calcium hydrate, sulfur and water raw materials are weighed into the duplicators 1A, 1B having been provided with agitators. From there they are forwarded via pipelines to the wet mill 2. In the mill the grain size of the suspension can be adjusted. The suspension thus prepared is fed by means of pump 3 to the column reactor 4 where its temperature is maintained at approximately 85° to 90° C. The suspension is fed into the lower part of the column reactor 4; during streaming upwards, the suspension is converted to a calcium polysulfide solution, in the meantime the water or the lime sulfur solution having been charged previously into the column reactor 4 will be displaced therefrom. The suspension is mixed with the agitator rotating in the column reactor. Due to the design of the stirring segments the backmixing is reduced to minimum. Water evaporated at reaction temperature is condensed in the reflux condenser 7 and is refluxed into the column reactor 4.

The lime sulfur solution sludge containing 10-30 wt. % solid residue and having a density of 1.25 to 1.32 g/cm$^3$ is allowed to flow through the stub on the upper part of the column reactor 4; the sludge discharged therefrom is cooled to room temperature in the cooler 8 and filtered by the filter unit separating the liquid and solid phases. The filtered lime sulfur solution is fed into the buffer tank 10. From the buffer tank 10 the lime sulfur solution, and from the storing tank 11 the surfactant, are led to the dispergator 14 operating in counterflow. Charging is performed in such manner that the lime sulfur solution and surface active material should be fed to the uppermost of the distributor trays 17 having been arranged in the dispergator, where the two material streams are converted to an emulsion by means of the six blade agitator 16. The emulsion thus obtained is led via the lower distributor tray to the lower part of the dispergator 14, wherefrom it arrives at the product tank 21 through the level control valve 20. By means of the liquid filler 22 the emulsion is discharged from the product tank 21.

In accordance with the invention in the course of producing the product, lime sulfur solution is mixed with surface active material and 0.5 to 25.0 wt. % oil based on the product. The surface active material can be of anionic or nonionic type and the combination thereof. From the applicable surface active materials we can advantageously use alkyl sulfonates, the salts of aliphatic sulfonic acids, the salts of aliphatic and aromatic sulfonic acids, fatty acid esters of polyhydric alcohols, polypropylene glycols, the adducts of ethylene oxide, alkylpolyoxyethyleneglycol ethers, ortophosphoric acid triesters, etc.

The oil suitable for the products can be a narrow distillate fraction of any mineral oil or oil of vegetable origin, with the boiling temperature in the range between 150° and 400° C., their nonsulfonable part amount to 60-90 wt. % with a density of 0.80 to 0.98 g/cm$^3$; closed cup flash point: 120°-160° C. Its kinematic viscosity amounts to $1-80.10^{-6} m^2 s^{-1}$ (1–10 E°), while the sulfur content is 0-2 wt. %.

The ratio of lime sulfur solution to oil is chosen as 1:1-1:9, advantageously 1:1-1:4. With these mixing ratios a stable product which can be well diluted with water can be obtained, this oily spray can be used as a washing spray, and with a properly chosen oil can be used against fungi and parasites even after blossoming.

The apparatus according to the invention is described in detail by means of the enclosed drawing wherein the sole figure is a schematic representation of the apparatus according to the invention.

The main parts of the apparatus are the feeding device 30, the mixing unit 40, as well as a second mixing unit 50.

The feeding device 30 includes the duplicators 1A, 1B provided with agitators, the wet mill 2, the charging pump 3 and they are all interconnected by pipes.

The mixing unit 40 comprises the cylindrical column reactor 4 which is provided with a heating jacket, with the stirrer shaft 5 and the stirrer drive motor 6, and the reflux condenser 7 connected to the reactor, as well as the cooler 8 connected to the column reactor 4, the filter unit 9 separating the liquid and solid phases which are interconnected with a pipe.

The second mixing unit 50 comprises the tank 11, the pump 13, the dispergator 14, which are also interconnected by pipes. The dispergator 14 contains the six bladed agitator 16 which is rotated by the motor 15, and the distributor trays 17. The dispergator 14 is connected to the tank 19 through the pump 18, the level control valve 20, the product tank 21 and the liquid filler 22 through pipes. In the vertical axis of the cylindrical case of the dispergator 14 there is a six bladed agitator 16, rotated by the motor 15. The distributor trays 17 arranged above each other and perpendicularly to the axis of the dispergator 14.

In operation of the apparatus, the preprocessed sludge of calcium hydrate, sulfur and water is led from the duplicators 1A, 1B provided with the agitators via the pipes into the wet mill 2. The mill 2 is designed to enable adjusting the desired grain size of the suspension. The suspension thus prepared is delivered by the charging pump 3 to the column reactor 3 which is at controlled temperature. The column reactor 4 is provided with a stirrer shaft 5 that is rotated by the motor 6. In the plane perpendicular to the stirrer shaft of the column reactor 4, there are stationary limiting discs fixed to the reactor and rotating discs fixed to the stirrer shaft 5. The column reactor 4 is divided into independent segments, and it can be adjusted by the axial positioning of the rotor discs rotating with the stirrer shaft 5 in a manner that undesirable backmixing can be avoided. Water having been evaporated from the column reactor 4 at reaction temperature is condensed in the reflux condenser 7 and recycled into the column reactor 4. A stud at the upper part of the reactor and serves to discharge the product and is connected by a pipe to the cooler 8 and the filter unit 9 which separates the liquid and the solid phases and through which the lime sulfur sludge containing 10-30 wt. % of solid by product and having a density of 1.25-1.32 g/cm$^3$ is conducted. Filtration can be performed with a settling centrifuge or a vacuum filter. Thereafter the clear lime sulfur solution is led into the buffer tank 10. From the buffer tank 10 the lime sulfur solution, from the tank 11 the surface active material, and from the tank 19 a nonfitotoxic oil are charged by means of the pumps 12, 12, 18, respectively, into the dispergator 14 which operates in a countercurrent. Lime sulfur solution and surface active material are fed to the upper distributing tray 17 arranged in the dispergator 14, while the nonfitoxic oil is fed under the lower distributor tray 17. The six bladed agitator 16 converts the material stream arriving from the two different directions into an emulsion. The emulsion that is obtained is led through the lower distributor trays 17 to the lower part of the apparatus, from where it is discharged into the product tank 21 through the level control valve 20 and from the product tank 21 it is discharged by the aid of the liquid filler 22.

The process according to the invention will be described in detail by means of some preferred examples:

EXAMPLE 1

CONTINUOUS PRODUCTION OF OILY SPRAY

A suspension of raw materials is prepared in a 10 liter mixer from the following materials: 5450 g industrial water; 2538 g powdered sulfur (floristella); 2030 g slaked lime (calcium hydrate) containing 90% Ca(OH)$_2$.

The solid substances having been previously mixed are homogenized in the mill 2 provided with the corundum disc. Grain size is reduced to under 100. The homogenous suspension is fed into the column reactor 4 having a volume of 900 g/cm$^3$ using sludge charging pump, with a uniform velocity of 480 g/cm$^3$, temperature is adjusted to 85°–95° C. and the speed of the agitator is set to 1200 rpm. The residence time calculated from the feeding velocity and the volume of the reactor amount to 2 hours, and when this period is the time needed for achieving steady state operation. The considered weight of the product samples recovered each hour is about 470–475 g. After filtering, the density of the lime sulfur solution is 1.30–1.32 g/cm$^3$ determined by a Mohr-Westphal type density measuring apparatus.

The weight of the wet solid material content is between 90 and 100 g. 375–380 g lime sulfur solution, having a density of 1.30–1.32 g/cm$^3$ can be recovered each hour. The apparatus is continuously operated for 8 hours, the filtered products recovered each hour are gathered and the total comes to 3000 g product having a density of 1.307 g/cm$^3$.

112.5 g surface active material of the polyoxyethylene alkyl ether type is added to the 3000 g collected lime sulfur solution and then the mixture is fed onto the uppermost distributor tray 17 of the dispergator 14 working in countercurrent, by means of one of the units of the charging pump of the twin piston type having a pumping velocity of 132 cm$^3$/hour. Simultaneously, oil is fed by means of the other charging unit of the pump into the space under the distributor tray 17, at a rate of 269 cm$^3$/hour. In the inner mixing space the speed of the six bladed agitator is kept within 3500–4200 rpm. Product is discharged through the overflow and level control having been arranged on the lowermost point of the dispergator 14 discharging at the rate of about 400 cm$^3$/hour. Average residence time of the components in the dispergator 14 operating in countercurrent at a volume of about 137 cm$^3$ is up to about 20 minutes.

Polysulfide sulfur content of the product produced according to the invention equals to 11.4 wt. % determined by the method in Ministry of Agriculture and Fisheries Tech. Bull. 1958/1, pages 41–42. Stability of storage and other physical and chemical properties of the product do not change in the customary packaging (polyethylene flask) at the ranges of ambient temperature of about −10° C. to +54° C. and storage time of two weeks over the longest period that was so far observed more than one year, the results obtained remain as mentioned above.

By using a spray of water, a product concentration of 0.5–5.0 w/w % was obtained and the stability of the emulsion met all the requirements. These included that after 24 hours the so-called "cream formation" did not exceed 1% and it could be reemulgated. In practice, the product is insensitive to the quantity of water and the temperature of the spray, and there are no unusual difficulties encountered in the technology of application. The emulsion can be easily sprayed onto, and adheres well to, the trees and to foliage.

EXAMPLE 2

BATCHWISE PRODUCTION OF A WASHING SPRAY 3000 g lime sulfur solution are produced by using a batchwise operated laboratory apparatus with approximately 1 liter volume so that cooking is performed with five identical charges using:

| | |
|---|---|
| industrial water | 331.0 g |
| sulfur powder floristella | 530.4 g |
| calcium hydroxide | 198.6 g |
| | 1040.0 g (about 800 ml) |

The content of the 1 liter flask provided with reflux condenser, thermometer and agitator is cautiously heated to 95° C. in an hour, while maintaining a rate of agitation of 900 rpm. This temperature is maintained for 10–20 minutes to avoid foaming and then the temperature is raised to 98°–102° C. and maintained at that level for 45 minutes. The reaction mixture is cooled to under 35° C. and filtered under vacuum. After repeating the aforementioned process five times, 3000 cm$^3$ of clear lime sulfur solution having a density of 1.302 g/cm$^3$ a total of 1290 g of solid byproduct is obtained, corresponding to 24.9 wt. % based on the total weighed quantity. It is clear that batchwise mode of operation requires nearly twice as much time than continuous operation (15 hours instead of 8 hours), when employing the same reactor volume.

The aqueous, oily, sulfur containing product, the 3000 cm$^3$ lime sulfur solution produced in the batchwise operated apparatus is subdivided into two equal parts. When processing the first part, 59.4 g emulsifier (1.5 wt. % based on the product) is added to the 1950 g lime sulfur solution. The solution then obtained is charged by the twin piston pump at a velocity of 155 cm$^3$/hour to the uppermost distributor tray of the dispergator 14 that is operated in a countercurrent. Sunflower oil is fed into the chamber below the lowest distributor tray of the dispergator 14 by means of the other charging unit of the pump. Dispersion is carried out at a speed of 3500 rpm. Product discharge is regulated so that a velocity of 365 cm$^3$/hour, the level of the emulsion above the uppermost tray is kept constant. Continuing the experiment for 10 hours, about 3600 cm$^3$ of oily product are obtained, containing 50% lime sulfur solution, well dilutable with water.

EXAMPLE 3

PRODUCTION OF OILY SULFUR CONTAINING SPRAY

To the other part (1950 g) of the lime sulfur solution prepared in the laboratory batch process of Example 2, 1287 g surface active material are added. Then the solution is homogenized and fed into the dispergator 14, by means of the twin piston pump at a rate of 324 cm$^3$/hour. Simultaneously sunflower oil is fed at a rate of 210 cm$^3$/hour, while the speed of the agitator is set to 3000 rpm. Product is discharged through the liquid level control; the yield is 530 cm$^3$/hour and the product can be easily diluted with water.

EXAMPLE 4

To 1950 g of lime sulfur solution produced in accordance with Example 1 and having a density of 1.30 g/cm$^3$ 156.25 g a polyoxyethylenealkyl ether surfactant is added; the homogenized solution is fed at a rate of 170 m$^3$/hour to the dispergator 14. Simultaneously 630 cm$^3$/hour spindle oil containing 80% nonsulfonatable part is added dispersion is performed continously, at a stirrer speed of 3200 rpm, for 10 hours. The 8000 g product obtained contains 25% lime sulfur solution, can be easily diluted with water and has a good shelf life, meeting all the requirements.

EXAMPLE 5

PRODUCTION OF AN OILY SPRAY

To 3000 g of the lime sulfur solution of a density 1.307 g/cm$^3$, produced in the continous process according to Example 1, 112.5 g of a polyoxyethylenealkyl ether surfactant is added; then the solution is fed into the dispergator at a rate of 134 cm$^3$/hour. Simultaneously, a paraffin oil mixture containing 85% nonsulfonatable part is added at a rate of 285 m$^3$/hour. The density of the oil mixture at 20° is 0.85 g/cm$^3$ and its kinetic viscosity is 18–20.16$^{-6}$m$^2$s$^{-1}$ (2.6–2.9 E°) at 20° C. Upon discharging the resulting product at a rate of 415–420 cm$^3$/hour, the product obtained in 17 hours is 7500 cm$^3$, it is viscous, contains 40% lime sulfur solution and can be easily diluted with water at a temperature between $-10°$ C. and $+54°$ C. and has a good shelf life.

EXAMPLE 6

PRODUCTION OF OILY SPRAY 97.5 g polyoxyethylenealkylether surfactant is continuously added, as in Example 1, to 1950 g lime sulfur solution having a density of 1.30 g/cm$^3$. The mixture is homogenized and then fed into the dispergator at a rate of 55.78 cm$^3$/hour. Simultaneously sunflower oil is added at a rate of 474.20 cm$^3$/hour during continous dispersing at a stirrer speed of 3600 rpm. The product is discharged while keeping the liquid level constant. The yield is 530 cm$^3$/hour, and the product can be easily diluted with water.

The advantage of the solution according to the invention is in the easy, quick and economical performance of the process. By use of the process a product can be produced at low cost from readily available raw materials. The product does not harm plants and can be widely used. It can be easily diluted and sprayed in compliance with prevailing practices.

A further advantageous feature is the more favorable fungicidal, insecticidal, acaricidal and ovicidal effect, compared to known lime sulfur solutions or oil products. A further advantage is that the lime sulfur solution and the surface active material considerably reduce possible detrimental accumulation of the oil component, at the same time the product has great storage stability.

The apparatus of the present invention operates in an energy saving fashion and it has flexible utilization capacity.

What we claim:

1. Apparatus for producing aqeueous, oily, sulfur containing products by producing a dispersion from a sulfur ingredient, oil and a surfactant, comprising wet grinding means for adjusting the particle size of a component of said sulfur ingredient, a reactor for producing said sulfur ingredient from its components at elevated temperature, a first pump for transporting the components of said sulfur ingredient to said reactor, a cooler for cooling the aqueous sulfur ingredient solution and solid residue from said reactor, separating means for separating the sulfur ingredient solution from the solid residue, dispersing means for emulsifying oil with the aid of a surfactant in said aqueous sulfur ingredient solution, containers each for storing said oil and said surfactant, second and third pumps for charging respectively oil and surfactant into said dispersing means, and means for recovering the aqueous, oily, sulfur containing emulsion product.

2. The apparatus of claim 1, wherein the reactor includes a reflux condenser for recovering water evaporated from the reactor.

3. The apparatus of claim 1, further comprising a buffer tank disposed between the reactor and the dispersing means for accomodating and evening out surges in the flow of the sulfur ingredient from the reactor, and means for transferring sulfur ingredient solution from said buffer tank to said dispersing means.

4. The apparatus of claim 1, wherein said means for recovering includes a tank connected from said dispersing means for storing the aqueous, oily, sulfur containing product.

* * * * *